United States Patent
Messick et al.

[11] Patent Number: 5,871,534
[45] Date of Patent: Feb. 16, 1999

[54] APPARATUS FOR TREATING PELVIC FLOOR DYSFUNCTIONS USING TRANSCUTANEOUS ELECTRICAL STIMULATION OF THE MUSCLES

[76] Inventors: Genevieve M. Messick, 2492 W. Lane Ave., Columbus, Ohio 43221; Phillip E. Muccio, 739 Kenwick Dr., Columbus, Ohio 43209

[21] Appl. No.: 111,537

[22] Filed: Jul. 8, 1998

[51] Int. Cl.⁶ .................................................. A61N 1/04
[52] U.S. Cl. ...................... 607/138; 607/149; 600/382; 600/390
[58] Field of Search ................... 607/115, 138, 607/143, 149, 152, 153, 41; 600/372, 382, 386, 390, 393, 546

[56] References Cited

U.S. PATENT DOCUMENTS

| | | | |
|---|---|---|---|
| 211,319 | 1/1879 | Carpender | 607/149 |
| 551,795 | 12/1895 | Spalding | 607/149 |
| 2,632,447 | 3/1953 | Dobes . | |
| 3,474,775 | 10/1969 | Johnson . | |
| 4,016,868 | 4/1977 | Allison . | |
| 4,092,985 | 6/1978 | Kaufman . | |
| 4,196,737 | 4/1980 | Bevilacqua . | |
| 4,202,344 | 5/1980 | Mills et al. | 600/390 |
| 4,300,575 | 11/1981 | Wilson . | |
| 4,381,012 | 4/1983 | Russek . | |
| 4,432,368 | 2/1984 | Russek | 607/149 |
| 4,458,696 | 7/1984 | Larimore . | |
| 4,580,572 | 4/1986 | Grasek . | |
| 4,583,547 | 4/1986 | Grasek . | |
| 4,919,148 | 4/1990 | Muccio . | |
| 5,313,952 | 5/1994 | Hoch | 600/390 |
| 5,450,845 | 9/1995 | Axelgaard | 607/149 |

FOREIGN PATENT DOCUMENTS 0 193 480 A1   9/1986   European Pat. Off. .

*Primary Examiner*—William E. Kamm
*Assistant Examiner*—Kennedy J. Schaetzle
*Attorney, Agent, or Firm*—Francis T. Kremblas, Jr.

[57] ABSTRACT

A device adapted to be worn by a human to provide transcutaneous neural stimulation or EMG monitoring useful for treating pelvic floor dysfunctions which includes a base portion comprising a flexible, nonabsorbent material layer configured to overlie the pelvic floor region of a human. The base is provided with an opening or slot disposed to overlie the anus or the vagina of the wearer to aid in proper positioning of the device. A pair of electrodes are mounted to the base in spaced relationship to one another and in surrounding and closely adjacent relationship to said slot. The electrodes preferably have a configuration adapted to overlie a sufficient portion of the pelvic floor region surrounding the anus of the wearer to effect a highly efficient stimulation of the pelvic floor muscles. Preferably, the base portion is securely held in position by a plurality of strap portions connected to the base which extend upwardly from the rear and front of the wearer for releasable connection to a holding member secured to or near the waist of the wearer.

8 Claims, 2 Drawing Sheets

APPARATUS FOR TREATING PELVIC FLOOR DYSFUNCTIONS USING TRANSCUTANEOUS ELECTRICAL STIMULATION OF THE MUSCLES

FIELD OF THE INVENTION

The present invention relates generally to treating pelvic floor dysfunction including urinary, fecal or associated disorders and particularly to a wearable device which includes electrodes which are accurately positioned in electrical contact with the skin surface about the pelvic floor area of the wearer to more advantageously provide for electrical stimulation and electromyography (hereinafter EMG) measurements related to specific muscles involved in treating pelvic floor dysfunctions.

BACKGROUND AND DESCRIPTION OF RELATED ART

Pelvic floor dysfunctions, such as urinary incontinence, for example, is a common problem in a large percentage of adults. Studies have shown that this problem can be effectively treated in a large percentage of the cases, however, various forms of urinary incontinence or other pelvic floor muscular dysfunctions require different forms of treatment or combinations thereof to increase the rate of success.

It has long been known that muscles can be electrically stimulated by the application of electrical impulses to the surface of the skin, referred to as transcutaneous electrical stimulation. For useful results, the proper positioning of the electrodes in relation to the nerve and associated muscle to be stimulated is very important.

Studies have been conducted using patch type surface electrodes which are adhesively attached to the body in the area of the pelvic floor for electrical stimulation of the pelvic floor muscles involved in treating urinary incontinence. The results of this study indicate such treatments can be useful to increase the success rate of combating urinary incontinence. In addition EMG measurements are desirable to monitor the course of progress during treatment.

However, the drawbacks to the prior method and means of treatment include significant irritation of the patient's skin, the need of relatively highly trained personnel to properly position the electrodes and/or properly instruct patients to position the electrodes and the fact that the configuration and nature of the patch type electrodes used, which are commercially widely available for general use, are not wholly satisfactory to provide efficient and effective treatment of the area involved.

Skin irritation of the patient from the adhesively applied electrode patches interferes with the treatment regimen required to effectively and comfortably treat a patient. In order to effectively treat a patient for these types of disorders, it is necessary to repeat the treatment several times over a significant number of days. In at least some instances, it is desirable to employ a continuous treatment over an interval of several hours in a day, which must also be repeated on subsequent days. The fact that many medical personnel have little or no training regarding the accurate positioning of the electrodes for treating pelvic floor dysfunctions, or for EMG monitoring, has limited the effective use of the prior method and means to a limited number of medical facilities which have a properly trained staff.

The above noted drawbacks have so limited the use of electrical stimulation techniques for treating these disorders that it is essentially not available to most of the patient population who may benefit from this form of treatment. Additionally, these drawbacks represent disincentives to the patient such that it is very difficult to obtain the patient cooperation necessary to conduct the full course of treatment required to be successful in resolving the problem.

There are presently available garments which carry a plurality of electrodes for electrical stimulation of different areas of the body, however, these garments are limited to generally large and more readily accessible areas of the body and are not suitable for use in treating pelvic floor dysfunctions, such as urinary incontinence. Such prior art is represented by U.S. Pat. No. 4,919,148 and the patents cited therein, for example.

SUMMARY OF THE INVENTION

The present invention relates to a wearable device for providing electrical stimulation and EMG monitoring of the muscles of the pelvic floor useful to treat pelvic floor dysfunctions. The device consists of a supporting base portion comprising, preferably, a tight knit material which is configured to overlie the pelvic floor muscles of the wearer. A pair of electrodes are mounted on the base in closely spaced but separated relationship and are configured to overlie a major area of the pelvic floor surrounding the anus of the wearer to assure effective contact with the nerves which control the pelvic floor muscles of interest.

An open space, preferably configured as a narrow slot, is provided in the base portion. One function of this slot is to prevent undesired electrical contact between the closely spaced electrodes or the conductive gel associated with an absorbent layer overlying each electrode. Further the slot represents an electrode positioning aid or guide when, preferably, it is disposed directly over the anus of the wearer to assure the base portion is properly positioned to dispose the electrodes in electrical contact with the area of the skin related to stimulating the desired muscles. In females, the slot may alternatively be positioned over the vaginal opening instead of the anal opening. Additionally, the slot provides access to the technical clinician to palpate the anal or vaginal passage, as applicable, of the wearer to ascertain the level of muscle contractions imparted by a given level of current being applied.

The supporting base preferably includes a pair of straps extending in opposing directions outwardly from the base which are adapted to be attached to a waist belt, or the like, releasably mounted on the wearer to secure the supporting base and the electrodes in an operative position. This combination forms an effective harness to not only carry the operative electrodes, but a convenient and easy to use means to adjustably position the electrodes in their proper location in a consistent manner.

In one preferred embodiment, each electrode is disposed in a respective one of a pair of pockets formed on the base in spaced relationship to one another. Each pocket includes an outer side comprising an absorbent material which may be readily wetted by a conventional conductive gel to increase the effectiveness of transmitting the desired electrical signals and to control contact of the gel to the desired limited area of skin.

Therefore it is an object of the present invention to provide a device of the type described to provide improved electrical stimulation and/or EMG monitoring of the pelvic floor muscles to enhance treatment of pelvic floor dysfunctions.

It is another object of the present invention to provide a device of the type described which is easily positioned upon the body of the wearer to accurately and consistently dispose the electrodes in contact with the desired body area and which requires very little medical education or training to do so.

It is another object of the present invention to provide a device of the type described which may be worn by the user during normal activity and still maintain the desired positioning of the electrodes in overlying contact with the area being treated. Therefore several daily repetitive treatments or a continuous extended daily treatment over several hours is made highly practical and more convenient for the patient.

It is a further object of the present invention to provide a device of the type described which accurately secures the position of the electrodes for electrical stimulation and/or EMG measurements in a difficult access region of the body in a relatively comfortable manner to encourage user compliance with the regimen of treatments necessary to aid in resolving the urinary incontinence problem.

Figure 1:
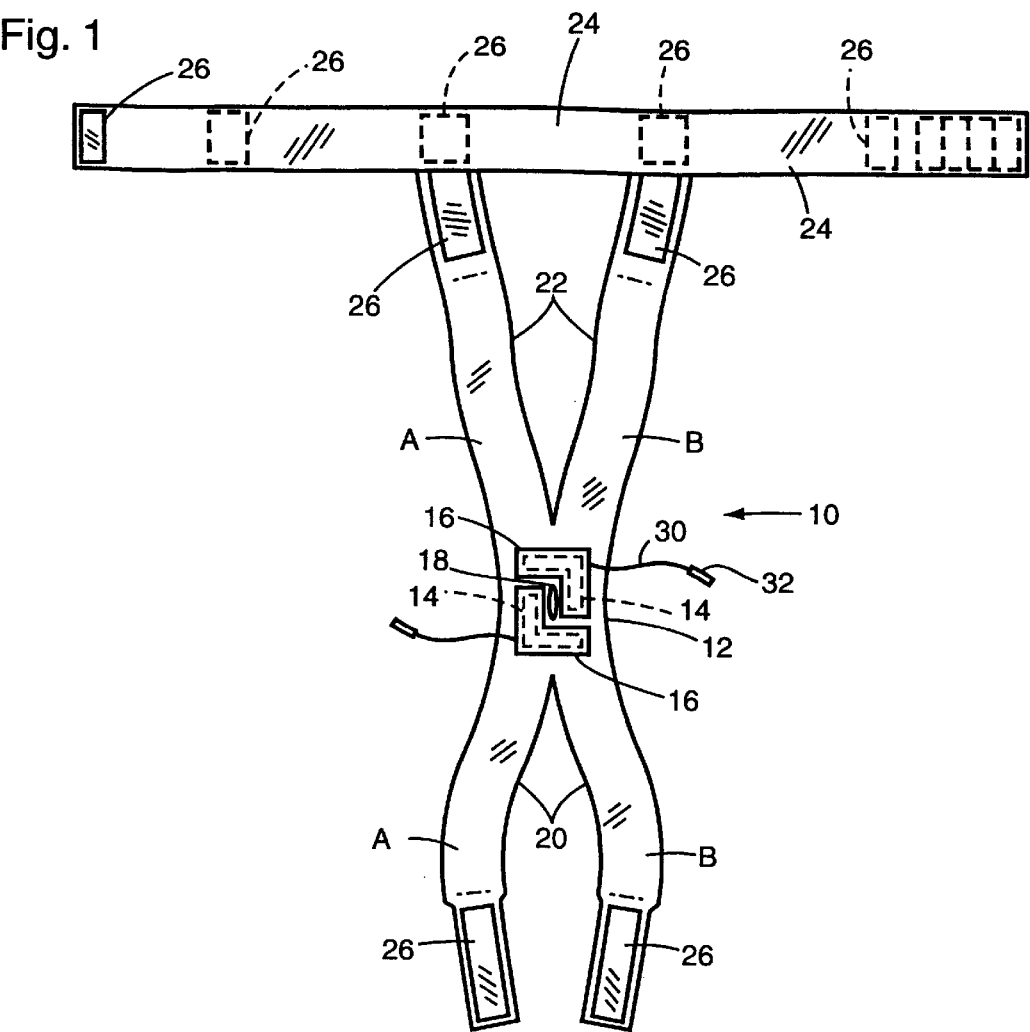
FIG. 1 is a plan view of the device for treating pelvic floor dysfunctions constructed in accordance with the present invention shown apart from its operative position as worn by a user.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. For example, the word "connected" or terms similar thereto are often used. They are not limited to direct connection but include connection through other mechanical means or electrical circuit elements where such connection is recognized as being equivalent by those skilled in the art.

BRIEF DESCRIPTION OF THE PREFERRED EMBODIMENT

It is to be understood that the term pelvic floor dysfunctions includes urinary incontinence, fecal and other associated disorders involving the muscles of the pelvic floor region. As described below herein, the preferred embodiment is described in connection with treating urinary incontinence, as an example, however treating other forms of pelvic floor dysfunctions using the apparatus described will be apparent to those skilled in the art.

Also, reference to the pelvic floor muscles as used herein is meant to include the anal sphincter muscles and the urethral sphincter muscles, as well as the pelvic muscles which support the bladder and urethra. Strengthening the latter muscle group is considered particularly important in many causes of urinary incontinence problems.

Figure 5:
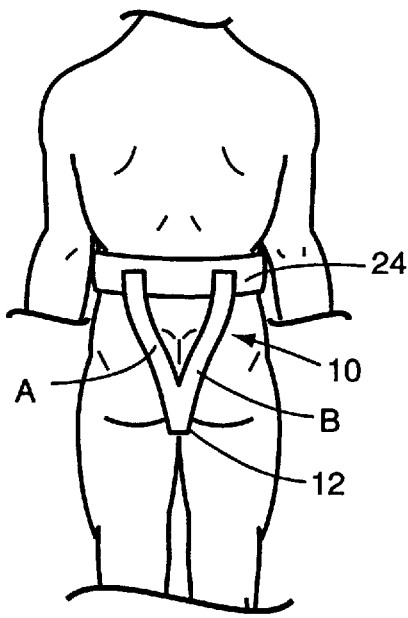
FIG. 5 is a rear view of the device shown in the operative position as worn by a user.
Figure 6:
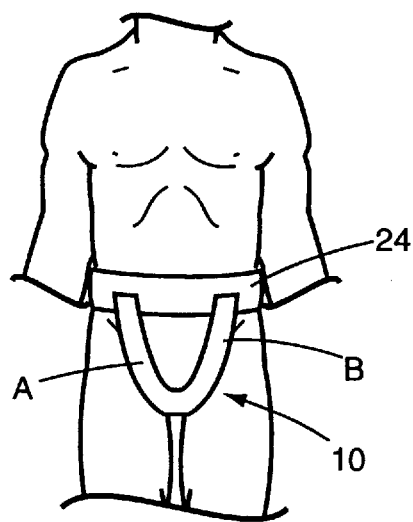
FIG. 6 is a front view of the device shown in the operative position as worn by a user.

FIGS. 1, 5 and 6 show a wearable device, indicated generally at 10, for treating urinary incontinence using electrical stimulation and/or EMG measurements which is constructed in accordance with the present invention.

The device includes an electrode supporting base area 12 configured to overlie the pelvic floor region of the wearer and is preferably made from a layer of flexible, non-conductive and generally non-absorbent material. A tight knit woven fabric material which is stretchable works well for purposes of the present invention. A blend of nylon and polyester, such as sold under the SPANDEX trademark, is quite suitable, although other types of materials would be expected to work well.

A pair of electrodes 14 are mounted to base 12 in closely spaced relationship to one another and each are covered by a layer of an absorbent material, such as felt layer 16, which readily absorbs liquid and can be thoroughly wetted by a conventional conductive fluid or gel. A suitable gel for purposes of the present invention is available under the trademark SIGNAGEL electrode gel, however, other appropriate conductive mediums, including solid forms under development or other types of conductive fluids, may also be used without departing from the spirit of the present invention. The electrodes 14 may be retained to base 12 by any conventional means which provides the necessary stability and the desired electrical contact with the targeted skin area via any suitable conductive medium.

The felt layer 16 preferably is sewn or otherwise securely fixed about its outer edges to the underlying material layer of base 12 to form a pocket or pocket-like structure preferably having a shape generally similar to the configuration of each electrode 14 which is disposed within a respective one of the pockets. The absorbent layer 16 is referred to as the outer side of the pocket and the underlying material of base 12 forms the inner side.

The felt layer is preferred because it can absorb a sufficient amount of the conductive fluid to provide good electrical contact between the skin and the electrode. Further, it tends to confine the conductive fluid to the area represented by the dimensions of the felt layer so reasonable control of the area of electrical contact between the skin and the electrode is maintained while wearing the device. Other forms of pockets or other configurations to operatively mount electrodes 14 on base 12 may also be used effectively to accomplish the desired result.

Figure 4:
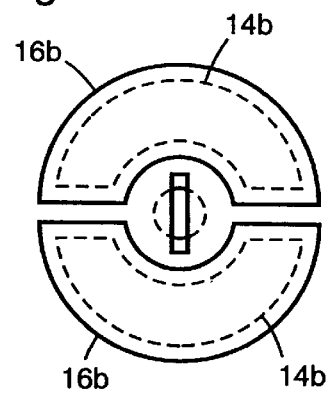
FIG. 4 is a partial plan view similar to FIG. 2 of another preferred embodiment diagrammatically illustrating another configuration of the electrodes on the supporting base.

Each electrode 14 may be of any conventional conductive material and preferably is made in a relatively flexible form. Such materials are well-known to those skilled in this art. Also each electrode 14 is configured to efficiently cover the surface area necessary to effectively stimulate the muscles of the pelvic floor area to be treated. One highly preferred configuration is a generally L-shape, such as shown in FIGS. 1 and 4, wherein each electrode is disposed in overlying and surrounding relationship to an opening or slot 18 provided in base 12.

Figure 2:
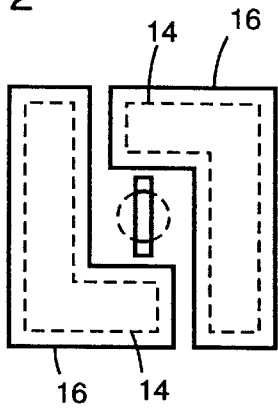
FIG. 2 is a partial plan view of a part of the device as shown in FIG. 1 diagrammatically illustrating the configuration of the electrodes and the preferred positioning thereof relative to a guide means and the anal area.
Figure 3:
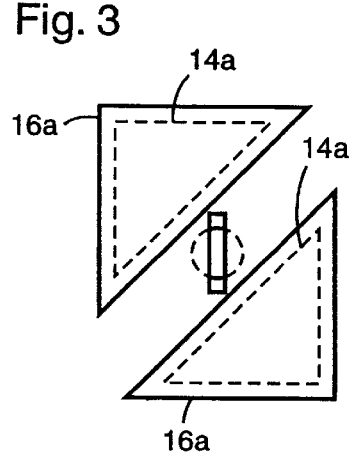
FIG. 3 is a partial plan view similar to FIG. 2 of another preferred embodiment diagrammatically illustrating a different configuration of the electrodes on the supporting base.

Since the proper positioning of the electrodes relative to contact with the desired area of skin is very important for electrical stimulation treatment as well as obtaining accurate EMG monitoring, slot 18 performs an important alignment function as described in detail later herein. Further, slot 18 allows closely adjacent spacing of the confronting edges of felt coverings 16 overlying each electrode 14 in order to maximize the area of electrical contact in the desired area, yet it provides an insulating space or barrier to prevent undesired electrical contact between the wetted felt coverings 16 which could short out the electrodes. The guide or alignment function of slot 18 which facilitates the proper positioning of electrodes 14 in overlying relationship to the desired area of the pelvic floor of the wearer renders the device very user friendly. One simply aligns slot 18 over one of the predetermined body cavities comprising either the anus or the vagina, where applicable. Then, by adjusting the attachment of straps 20 and 22 to a holder, such as waist belt 24, at an appropriate length, the desired positioning of the electrodes 14 and felt pads 16 is maintained. Aligning slot 18 in overlying relationship to one of the above-mentioned pre-selected body cavities, assures correct positioning has been made and/or is being maintained during the treatment interval. The dotted circle 19, in FIGS. 2–4 diagrammatically illustrates the anus of the wearer relative to a desired position of slot 18.

Providing a guide means, such as slot 18, in combination with the manner in which base 12 is secured in position, greatly increases the effectiveness of treatment. Further proper positioning assures that the device is more comfortable to wear. These features reduce the need for a high degree of education or training regarding this form of treatment by medical personnel aiding the patient. With minimal instructions, a lay person, including the user would be able to correctly mount the device in the proper position.

This aspect of convenient and facile positioning and comfortable wearability offers greatly expanded opportunity for use and successful treatment of urinary incontinence or other pelvic floor dysfunctions using electrical stimulation compared to the prior methods and means. In addition, the relative comfort provided to the wearer is very important to encourage cooperation of the patient in properly conducting the regimen of treatments for successful re-training of the muscles involved in the particular pelvic floor dysfunction involved.

Further, slot 18 provides convenient access for palpation of either the vaginal passage or anal passage, according to the design of the apparatus, for clinical confirmation of the appropriate functional level of muscular contraction being effected by a given level of current application to the electrodes. Appropriate adjustment of the level of electrical current applied can then be assured in a simple manner. However, it is recommended that EMG monitoring also should be used at appropriate intervals to more precisely measure the functional level of muscular contraction being effected by the level of electrical stimulation being applied.

Now referring to FIGS. 1, 5 and 6, base 12 includes front and rear elongate strap portions 20 and 22 respectively, each of which is preferably formed into two separate legs, such as "A" and "B". Straps 20 and 22 are adapted to reach upwardly from the wearers crouch area to make a releasably fixed connection to a support or holding member, such as belt portion 24, which is secured around the waist of the wearer. Each leg "A" and "B" of straps 20 and 22 preferably diverge from one another for attachment in spaced relationship about the circumference of belt 24 to better secure and stabilize the position of base 12 and hence, electrodes 14, in the desired position relative to the wearer's body and form an effective wearable harness-like structure to hold electrodes 14 in the desired position.

Belt 24 is preferably made of an elastic material which can be snugly and securely held in position around the waist of the wearer. Complementing VELCRO attaching means, such as indicated at 26, are preferably used to releasably tighten belt 24 in a secure position on the wearer and to secure the strap portions "A" and "B" to belt 24. However, other suitable well-known releasable attaching means can be used without departing from the spirit of the present invention. Such means preferably provide for easily adjusting the effective length of the strap portions to permit the base 12 to be held snugly against the wearer to accommodate persons of varying size. The elastic or resilient nature of the material used for base 12 and, if desired, strap portions 20 and 22, may also aid in adapting the device to comfortably and properly fit persons of different statures and sizes.

Further, a pair of suspenders or the like, not shown, could be used with or without belt 24 in order to support the desired position of strap portions 20 and 22 and thus base portion 12.

Now referring specifically to FIGS. 3 and 4, two modified electrode configurations are illustrated for use in the device of the present invention. In FIG. 5, the modified configuration of electrodes 14a comprises a pair of generally triangular shapes which are tilted or offset relative to a line longitudinally directed through slot 18 so as to overlie a substantial area to each side, above, below and closely adjacent to the anus of the wearer.

If desired, it should be understood that for females, slot 18 could be designed to be aligned over the vaginal opening, instead of the anus, with an appropriate re-positioning and or selection of the shape of the electrodes 14 and pockets 16 to accommodate this change of position to obtain effective coverage of the pelvic floor area. This modification would provide the same effect of assuring correct alignment of electrodes 14 over the desired pelvic floor area and also permit access to palpate the vaginal passage to check the level of muscular contractions being affected.

With reference to FIG. 4, a pair of generally semi-circular shaped electrodes 14b are shown which are configured to overlie a major portion of skin area of the pelvic floor area surrounding the anus of the wearer. It is noted that a generally U-shape or horseshoe shape as well as confronting C-shapes for electrodes 14 and felt coverings 16 could also be effectively used in a similar fashion to the semi-circular shape shown in FIG. 4 to obtain a desirable amount of surface contact with the desired area in this body region. Also such shapes could be easily rotated 90 degrees from that shown in FIG. 6 to accommodate positioning slot 18 over the vagina of a female user.

In the same manner for all the embodiments shown, a conventional wire 30 may be attached to each electrode 14 and extended outwardly from the pocket formed between felt coverings 16 and the underlying material of base portion 12. The outer end of each wire 30 may be provided with a female receptacle 32 for a conventional pin connector to conveniently connect a respective electrode to a source of electrical stimulation or to other electronically operated measuring and recording devices, such as for EMG monitoring, for example. The means for providing and operating such electrical sources are conventional and well-known, therefore they need not be shown or described in detail for one of ordinary skill in the art to understand how to make and use the present invention for its intended purpose.

In view of the foregoing description, it should be understood that the device described provides a convenient and an easy to use means for transcutaneous electrical muscle stimulation and/or EMG monitoring of the muscles of the pelvic floor region for treating pelvic floor dysfunctions, including urinary incontinence. It provides a vast improvement to the adhesively applied electrodes and allows secure, accurate and consistent placement of the electrodes in this difficult to access region of the body. It should be pointed out that consistent placement is important to both stimulation of the proper muscles and particularly to EMG monitoring. The present invention also provides a relatively high degree of comfort and reduces the inconvenience to the patient undergoing such treatment.

Further, it solves the problem of interruptions of treatments due to patient skin irritation caused by prior methods and means which also increases the tendency of patients to refuse to continue treatment. Additionally the present invention allows the patient a high degree of normal activity while wearing the device so as to reduce the inconvenience of a daily treatment regimen.

Slot 18 provides a means for facile and accurate alignment of the base 12 to assure accurate positioning of electrodes 14 by personnel lacking extensive education and training in this form of treatment and provides access to the pre-selected body cavity for palpation by a trained clinician. From the foregoing description it should be understood that the present invention promotes more widespread access to such treatment compared to prior methods and means.

It should also be pointed out that an electrical stimulation regimen and EMG monitoring may be combined with other forms of treating behavioral aspects of urinary incontinence. Such other forms include pelvic floor exercises as prescribed by a knowledgeable physician or therapist. Such a combination is believed to maximize the success rate of overcoming many of the major causes of urinary incontinence or other pelvic floor dysfunctions, excepting of course, those due to non-reversible causes.

While certain preferred embodiments of the present invention have been disclosed in detail, it is to be understood that various modifications may be adopted without departing from the spirit of the invention or scope of the following claims.

We claim:

1. A wearable device for providing transcutaneous neural muscular stimulation or EMG monitoring of the human pelvic floor muscles useful for treating pelvic floor dysfunctions, comprising in combination:

a) a base portion configured to be releasably fixed in overlying relationship to the pelvic floor region of a human comprising a layer of non-conductive, flexible, non-absorbent material and including an opening disposed in said base portion to expose a body cavity located closely adjacent to the pelvic floor area of a human when the base portion is operatively positioned on the human;

b) a pair of electrodes mounted in spaced relationship to one another on said base portion and disposed in closely adjacent relationship to said opening, each of said electrodes having a shape configured to overlie an area generally overlying the human pelvic floor area when said opening is aligned over one of said body cavities.

2. The device defined in claim 1 wherein, each of said electrodes are disposed within a different pocket provided on said base portion and spaced from one another in closely adjacent relationship to said opening, each of said pockets having an outwardly facing side comprising a layer of a readily wetted, absorbent material, said outwardly facing side having a configuration generally conforming to the configuration of the electrodes disposed therein.

3. The device defined in claim 2 wherein each of said pockets include an inner side comprising a non-absorbent material.

4. The device defined in claim 1, further including at least one pair of straps, one of said pair connected to a rearwardly directed portion of said base portion and the other of said pair connected to a forwardly directed portion, each of said straps configured to extend upwardly from said pelvic floor region for releasably fixed attachment to a holding member secured to the torso of a wearer to hold said base area in overlying relationship to the pelvic floor region of said wearer with said opening aligned over said body cavity of said wearer.

5. The device defined in claim 4 wherein the upper end of each strap of said pair of straps includes a pair of diverging end portions, each of said end portions being releasably fixed to said holding member at horizontally spaced locations.

6. The device defined in claim 1, wherein each of said electrodes have an L-shaped configuration and are disposed in opposing alignment in relation to one another to generally surround said opening in said base portion.

7. The device defined in claim 1 wherein each of said electrodes have an arcuate configuration and a pair of ends, each of said ends of each electrode being disposed in confronting relationship with one of the ends of the other electrode to define an open space between said electrodes disposed in a predetermined spaced relationship relative to said opening in said base.

8. The device defined in claim 1 wherein said opening in said base has a narrow slot-like configuration.

* * * * *